United States Patent

Schwotzer et al.

[11] Patent Number: 6,007,904
[45] Date of Patent: Dec. 28, 1999

[54] OPTICAL SENSOR ELEMENT

[75] Inventors: Günter Schwotzer, Dorndorf-Steudnitz; Reinhardt Willsch, Jena, both of Germany

[73] Assignees: Bartec Componenete und Systeme GmbH, Gotteszell, Germany; Institut fuer Physikalische Hochtechnologie e.V., Jena, Germany

[21] Appl. No.: 08/860,771
[22] PCT Filed: Nov. 22, 1996
[86] PCT No.: PCT/EP96/05155
 § 371 Date: Jul. 3, 1997
 § 102(e) Date: Jul. 3, 1997
[87] PCT Pub. No.: WO97/21092
 PCT Pub. Date: Jun. 12, 1997

[30] Foreign Application Priority Data

Dec. 6, 1995 [DE] Germany .......................... 195 45 414

[51] Int. Cl.⁶ ............................. G01N 21/41; G01N 21/75
[52] U.S. Cl. .................. 428/306.6; 428/216; 428/307.3; 428/308.4; 428/315.7; 428/315.9
[58] Field of Search .............................. 428/306.6, 307.3, 428/308.4, 315.7, 315.9, 212, 216

[56] References Cited

U.S. PATENT DOCUMENTS 4,641,524  2/1987  Tarvin ....................................... 73/335

FOREIGN PATENT DOCUMENTS

| 0536656A1 | 4/1993 | European Pat. Off. . |
| 0538664A2 | 4/1993 | European Pat. Off. . |
| 0598340A1 | 5/1994 | European Pat. Off. . |
| 0598341A1 | 5/1994 | European Pat. Off. . |
| 3832185A1 | 3/1990 | Germany . |
| WO 83/02327 | 7/1983 | WIPO . |

OTHER PUBLICATIONS

M. Tabacco et al.: "Chemical Sensors for Environmental Monitoring"; SPIE vol. 1587 Chemical, Biochemical and Environmental Fiber Sensors III (1991) / 271–277.

Patent Abstracts of Japan vol. 11, No. 319 (P–627) [2766], Oct. 17, 1987 & JP 62 108133 A (Fujitsu Ltd), May 19, 1987, see abstract.

J.P. Conzen, et al.: "Characterization of a Fiber–Optic Evanescent Wave Absorbance Sensor for Nonpolar Organic Compounds"; Applied Spectroscopy vol. 47, No. 6 (1993) 753–763.

C. Ronot, et al.: "Detection of chemical vapours with a specifically coated optical fibre sensor"; Sensors and Actuators B, 11 (1993) 375–381.

H. Koch: Optische Untersuchungen zur Wasserdampfsorption in Aufdampfschichten phys. stat. sol. 12 (1965) 533–543.

Primary Examiner—D. S. Nakarani
Attorney, Agent, or Firm—Jordan and Hamburg LLP.

[57] ABSTRACT

An optical sensor element for detecting organic compounds, particularly hydrocarbon. The sensor element permits the selective detection of substances by use of units which produce spectral displacements. This is realized by employing a spectral band filter, which comprises at least one layer of variable optical thickness of $\lambda/4$ and $\lambda/2$, respectively, or a multiple thereof, and said layer exhibits hydrophobic properties and includes organic affinity groups, the selection of which is adaptable to the substances to be detected.

5 Claims, 3 Drawing Sheets

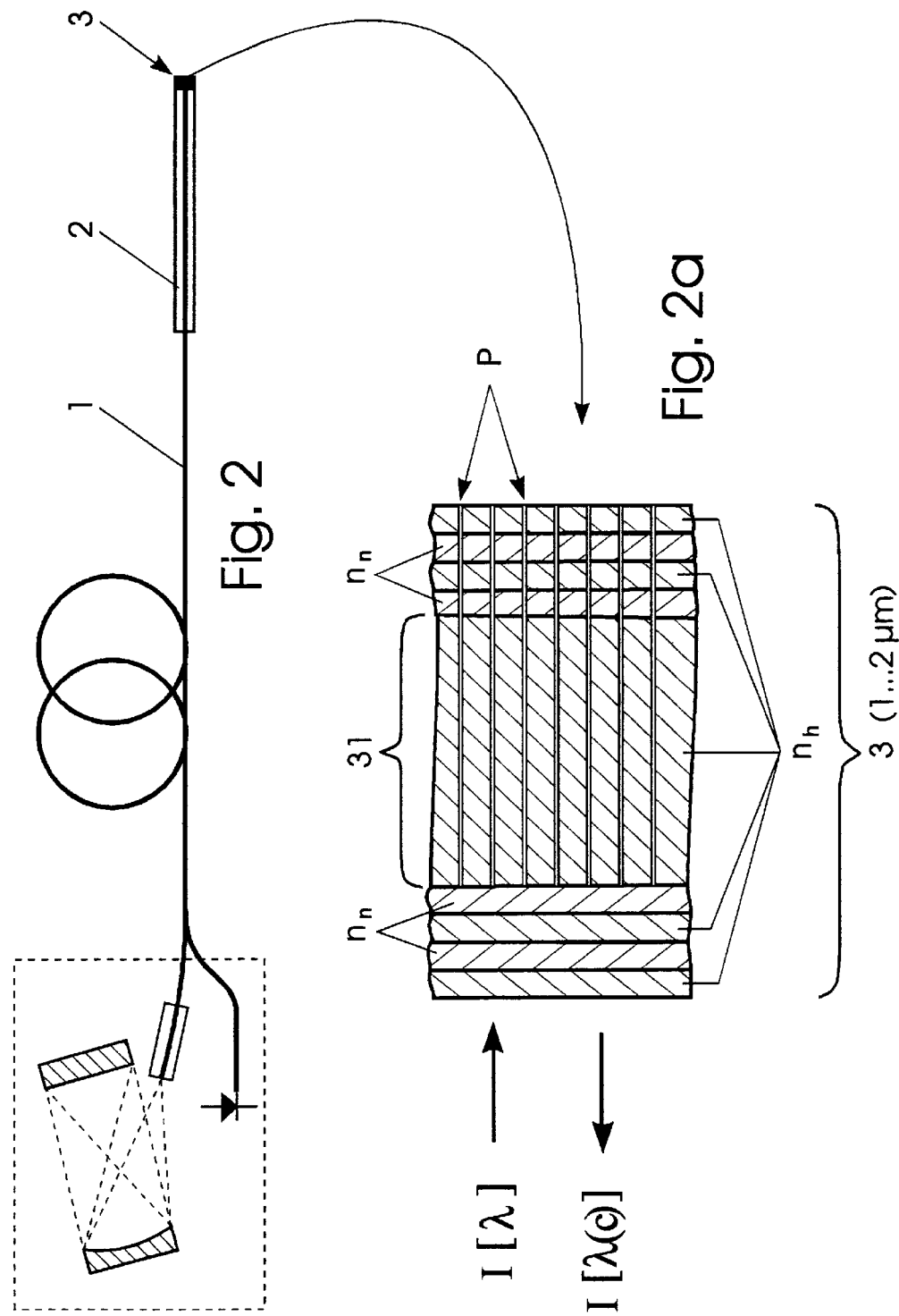

OPTICAL SENSOR ELEMENT

BACKGROUND OF THE INVENTION

The invention relates to an optical sensor element for detecting organic compounds, particularly hydrocarbon, which can be utilized, for example, in environmental and health protection.

Hydrocarbon may pollute the environment and may be harmful to human health. Hence, the measurement of hydrocarbon is an important task. Conventional methods for detecting hydrocarbon are chromatography, IR-absorption methods, acousto-optic measuring methods, heat conductivity measurements, heat effect measurements of the catalytic decomposition of the hydrocarbons, or electrolytic conductivity measurements.

The first three measurement methods use expensive equipment and only permit application in laboratories. The other methods are suited for embodying measuring feelers which can be installed at different places in the environment or industrial processes. Their lifetime is short when subject to corrosive ambiance. Since their function relies on electrical principles they are, when used in an explosive environment, only applicable with explosion-protective measures. The measuring and amplifier electronic, respectively, has to be installed in the direct vicinity of the measuring feeler. In contrast thereto, fiber-optical sensors conventionally do not require any additional explosion-protective measures and they permit greater distances, up to the kilometer range, between the measuring location and the signal evaluation (remote sensing) due to the extremely interference-safe and low attenuated measuring signal transmittance via light cable. Thus, in contrast to electronic sensors, applications become feasible even under adverse environmental conditions and at measuring places difficult to access. Recently, solutions of fiber-optical sensors have become known for detecting hydrocarbon.

So it has been proposed, for example, to make light cables out of porous glass and, in a next step, to secure a chemical species, which is sensitive towards the substances to be detected to the glass surface [M. Tabacco et al: "Chemical Sensors for Environmental monitoring"; SPIE Vol. 1587 Chemical, Biochemical and Environmental Fiber Sensors III (1991) 271]. However, a such prepared porous fiber is scarcely suited as a sensor in practical use since it is very fragile. Furthermore, with this sensor principle, the intensity measurements on light conducting fibers are an ill suited means to ensure a stable and quantitatively reliable detection of the concentration of the substances to be detected since. Any variation of the light intensity of the light source or of the fiber feed to the sensor distort the measuring signal.

Other examples use a light conducting fiber which is composed of a quartz glass core and an optical coat made of silicon [J. P. Conzen, et al: Characterization of a Fiber-Optic Evanescent Wave Absorbance Sensor for Nonpolar Organic Compounds"; Applied Spectroscopy Vol. 47, 6 (1993) 753 or C. Ronot, et al: "Detection of chemical vapours with a specifically coated optical fibre sensor"; Sensors and actuators B, 11 (1993) 375–381]. The silicon coat protects the fiber core against water and other polar substances. Organic compounds, however, such as hydrocarbon compounds, are able to diffuse into the silicon coat. Refractive index variations, swelling and optical absorption variations may result. These variations affect the transmission of the light conducting fiber, since a definite portion of the light conducted in the light conducting fiber also enters into the optical coat as a so-called evanescent wave where it is subject to the variations. Sensors based upon these effects mostly require light conducting fibers of several meters to ensure a sufficient sensor sensitivity and, hence, some space, since the evanescent light portion only makes a small part of the entire light conducted. In this case, it is also true that the principle of transmission measurement on light conducting fiber sensors is disadvantageous with respect to the stability and reproducibility of the sensors. Such disadvantages may deteriorate the advantages otherwise inherent in optical fiber sensors, such as explosion safety, immunity to electromagnetic interference fields, optimal electric potential splitting or bridging of great distances between measuring place and the location of the electronic signal evaluation and, thus, may prevent practical use.

It is further known that a safe and non-distorted transmission of optical sensor signals is feasible with light conducting fibers, even over wide distances, when the measuring information is transmitted as a spectrally encoded optical signal wherein the variations of the measuring information are rendered measurable as spectral displacements of maxima or minima of the light intensity. An example of such a principle is a fiber-optical moisture sensor [EP 0 536 656 A1] and associated method for signal evaluation [EP 0 538 664 A2]. The proper moisture-sensitive element of the fiber-optical moisture sensor is an optical narrow-band filter constituted of a stack of sandwiched optical layers selected from inorganic dielectric material with alternating high and low optical refractive index. The optical layer thickness always is a multiple quarter and a multiple half, respectively, of an adjustable mean working wavelength of the measuring light. It has been known that such layers, when manufactured by vacuum deposition, are porous and, in the presence of water vapor in the ambiance, can take up water [H. Koch: "Optische Untersuchungen zur Wasserdampfsorption in Aufdampfschichten" phys. stat. sol. 12 (1965) 533–543]. The optical refractive indexes of the individual layers vary with the absorption of water and the filter spectrum is displaced towards longer wavelengths.

The spectral displacements of the filter spectra are very precisely measurable even over wide light conducting fiber paths and fiber optical moisture sensors provided with such sandwich stacks permit a very reliable evaluation.

However, such layers according to the state of the art are only sensitive with respect to water vapor, apart from small undesired transverse sensitivities of other vapors such as, for example, alcoholic vapor or ammonia.

It is an object of the invention to provide an optical sensor element for detecting organic compounds, particularly hydrocarbon, that permits the selective detection of the latter by use of units which produce spectral displacements.

SUMMARY OF INVENTION

The invention provides at least one optical layer, which is part of a spectral band filter constituted of a plurality of λ/4 and λ/2 layers, respectively, and which possesses defined characteristics with respect to the affinity relative to at least one substance to be detected. The characteristics have the effect that the optical thickness of a layer and a stack of such layers, respectively, is subject to variations.

BRIEF DESCRIPTION OF THE DRAWINGS

FIG. 2 shows application of a stack of layers according to the invention which is used as a sensor head of a fiber optical detector operating in reflection mode, FIG. 2a is a detailed schematical representation of the stack of layers according to FIG. 2.

DETAILED DESCRIPTION OF THE INVENTION

The starting point for all further considerations is a spectral band filter of a plurality of optical thin layers having a thickness of $\lambda/4$ and $\lambda/2$, respectively, or a multiple thereof in which layers are arranged alternatingly high refracting ($n_h$) and low refracting ($n_n$) with respect to the mean working wavelength of the measuring light utilized. It is of no consequence within the scope of the invention whether the spectral band filter is embodied as a transmission filter or as a reflection filter, an edge-type filter, a narrow-band filter, etc. The filter includes at least one layer of variable optical thickness (which is the product of refractive index and geometrical thickness) of $\lambda/4$ and $\lambda/2$, respectively, or a multiple thereof and which exhibits hydrophobic properties and includes organic affinity groups, the selection of which is adaptable to the compounds to be detected, and is exclusively constituted of such layers, respectively.

In a first embodiment, as shown in FIG. 2 and 2a a layer 31 of a spectral filter layer system according to the invention is a dielectric inorganic material, for example, of at least one metal oxide which, due to its manufacture, is provided with pores P of a maximum size up to 10 nm. Such a size of the pores ensures that the optical layer appears optically homogeneous and substantially no light scattering occurs. The layer is enclosed on both sides by alternating high refracting $n_h$ and low refracting $n_n$ thin films in the form of a reflection filter wherein, on the detection side (on the right side of FIG. 2a), the reflection filter layers are also provided with pores which are interconnected with the pores in the layer 31 to permit the entry of substances to be detected. According to the invention, at least the pores in the layer 31—the surfaces of the pores and also the surface of the layer 31 naturally are extremely hydrophilic—are covered by molecules which render the character of the surface strongly hydrophobic. Such a deposit is obtained by, for example, silylation. Organosilane compounds, for example, are suited for it, which have the general chemical formula $R_ZSiX_{(4-Z)}$ with ($1 \leq Z \leq 4$). X designates a hydrolysable group, such as an alkoxy-group, or a halogen, such as chlorine, and R stands for a non-hydrolysable organic radical which is adapted to provide the pore surface with a special functional property, in the sense of the invention, in particular a hydrophobic property. Methoxy-($-OCH_3$) and the ethoxy-($OCH_2CH_3$)-group are examples for the alkoxy-groups.

Figure 1A:
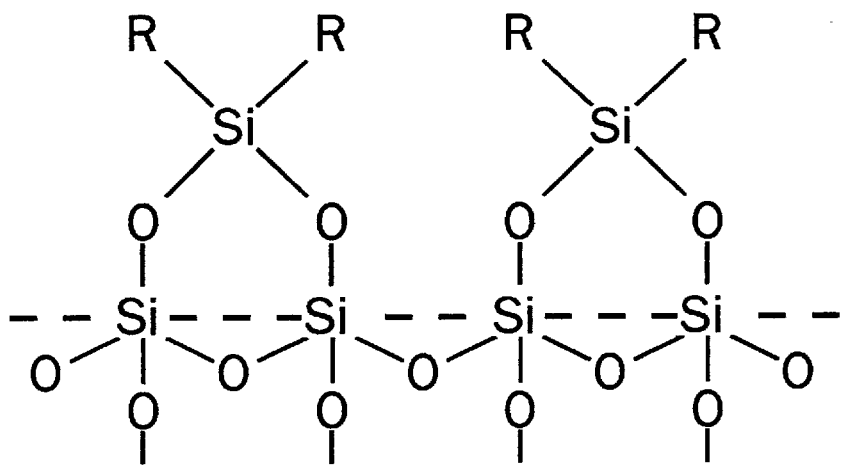
FIG. 1a and FIG. 1b show possible deposits and their formation on porous layers according to the invention.
Figure 1B:
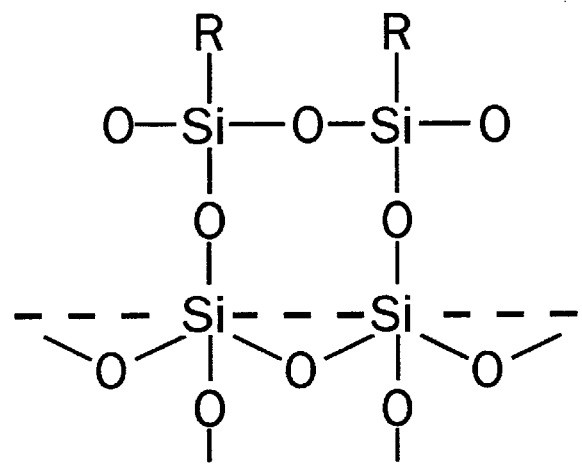

By chemical reactions of such an organosilane compound with a hydrated metal oxide surface, the hydrolysable groups X react with the hydrogen of the hydroxyl groups on the metal oxide surface and are separated, so that the silicon with its functional group R is chemically combined with the metal oxide surface. Feasible surface formations of the kind mentioned are indicated in FIGS. 1a and 1b.

In a simple example, methylchlorine-silane, such as $(CH_3)_2SiCl_2$, is substituted as an organosilane compound. Since methylchlorine-silane boils between 57° C. and 70° C., the operation preferably takes place slightly above these temperatures and permits the vapor to react with the pore surfaces. During operation, a thin methylpoly-siloxan film deposits on the interior of the pores, while the liberated hydrogen chloride evaporates.

A surface deposit produced in this manner has a distinctive affinity towards non-polar and low-polar molecules so that a moistening occurs with such compounds, whereas water is repelled. Since the inventively coated pore surfaces are strongly concave, a vapor pressure reduction in the moistening liquid takes place. The greater the reduction the more distinct is the moistening power and the smaller are the pores. Hence, the vapor pressure reduction leads to a condensation of vapors in the pores, these vapors originate from a gas mixture which, for example, contains, inter alia, condensable non-polar vapors, such as organic solvent vapors or other condensable hydrocarbon compounds. The cavities of the individual pores which were initially filled with gas and vapor, respectively, are now filled with a liquid. Thus, the optical refractive index of the porous layer increases and, hence, its optical thickness.

In order to render the variations of the optical thickness of the layer measurable, the latter is so adjusted in the course of manufacture of the layer that it equals a quarter or a half of a mean working wavelength of a selected light spectrum or an integral multiple thereof. According to optical relations, known to one skilled in the art, optical layers show transmission or reflection maxima at these wavelengths. The original mean working wavelength is displaced proportionally to the optical variation of thickness when an inventive variation of the optical thickness takes place due to condensation of non-polar vapors in the pores. It is feasible to evaluate such spectral displacements with high precision and reliability by utilizing spectral measuring techniques as disclosed in EP 0 538 664 A2.

In order to set the transmission maxima or minima favorable for evaluation to obtain a still higher contrast, it is advantageous to provide the porous layer and the stack of layers, respectively, on both sides with semi-transmissive reflecting areas. According to the invention, the layers are so embodied that at least the reflecting areas on one side are also porous and all pores of the mean porous sensitive layer, which substantially determines the working wavelength, have access to the outside through which the vapor molecules may enter the pores from ambiance and vice versa. It is feasible to make the reflecting areas of dielectric matter the optical thickness of which corresponds to a quarter of the light wavelength or of partially transmissive metallic matter.

Figure 3:
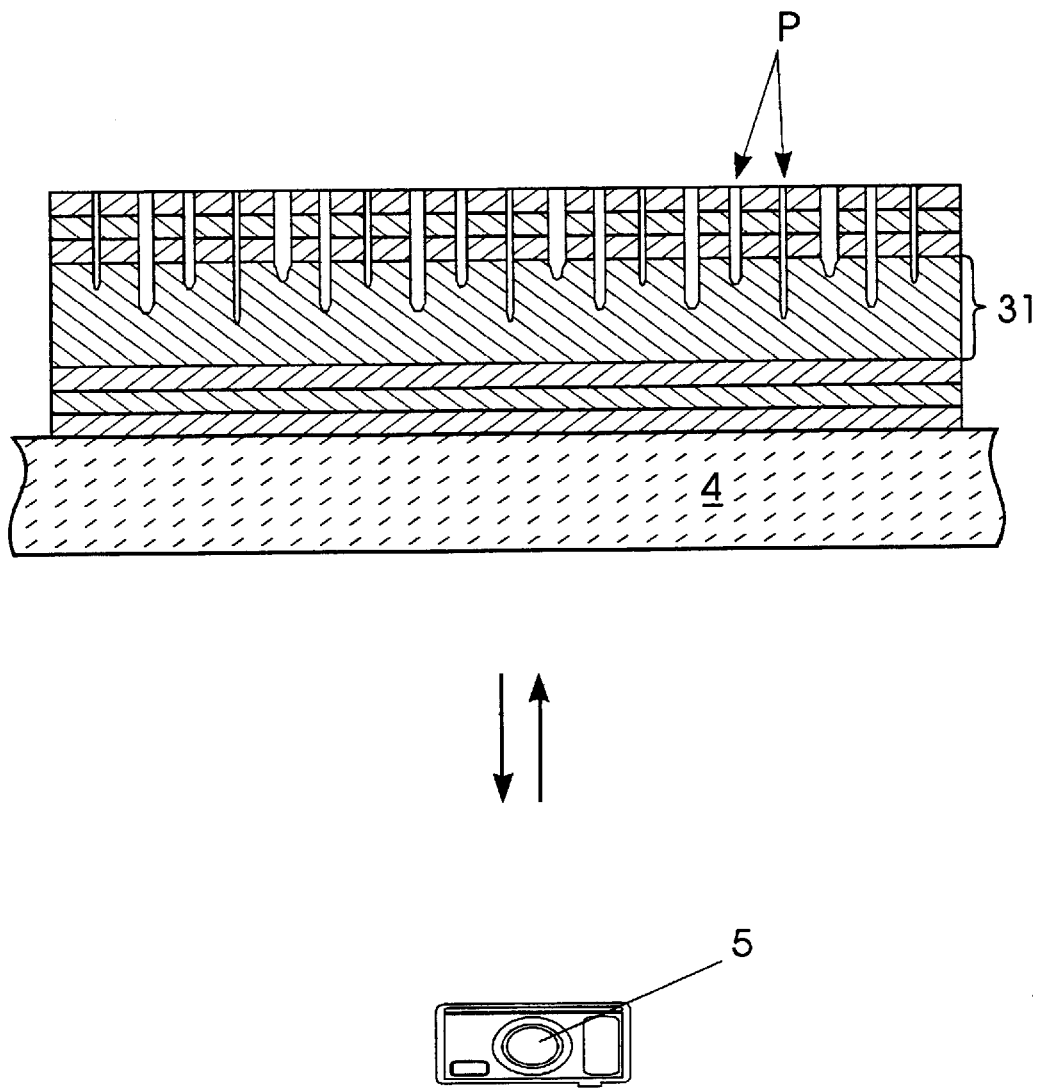
FIG. 3 shows a possible application of an extended stack of layers according to the invention, which are scanned in transmission by, for example, a CCD-camera.

In a further embodiment of the inventive sensor element it is feasible to non-displaceably connect the spectral filter layer system 3 via the sensing head 2 to the end faces of light conducting fibers 1, as shown in FIG. 2a, or directly attach them to the former. The light conducting fibers 1 are employed to feed the illumination I [$\lambda$] into the layer system 3 and to feed back the filtered light I [$\lambda$(C)] to an optical evaluation unit indicated in FIG. 2 by a dashed-line frame, wherein C is the concentration of the substances to be detected. It also lies within the scope of the invention to embody the spectral filter layer system 3, 31 as an extended spatial plate attached to a transparent mount 4 (as shown in FIG. 3) and to carry out the spectral evaluation at a remote place, for example, via a CCD-camera 5.

It lies, of course, within the scope of the invention to use others than the described organosilane compounds in order to either increase the temperature stability of the siloxane films or to vary the polar characteristic or to enhance the selectivity of the interaction with special molecules.

Particularly, the dielectric inorganic basic matter for the porous layer can be replaced by organic matter, the molecules of which form cage-like cavities, such as cyclodextrin, wherein the selectivity with respect to certain molecules is obtainable by the conformity of the size of said molecules with the size of the molecular cage.

Since the example described concerns covering surfaces of micro-pores with hydrophobic molecules the application of such modified micro-porous layers for detecting substances with non-polar molecules is not restricted to a gaseous ambiance. It is also feasible to detect non-polar hydrocarbon dissolved in water, as far as there exists a condensable phase.

It is a feature of the invention that, by depositing a thin layer on the pore surface, the latter is provided with a property which decisively determines the capability to attach matter depending on the polar or non-polar character of the molecule, that is, of the wettability. Thus, for example, it is feasible to replace the methyl-groups used in the above example by other groups, preferably bound to silicon, such as phenyl groups or amino groups to modify the selectivity of the sensors with respect to certain hydrocarbons, amines and others. A phenyl group, for example, considerably increases the desired hydrophobic effect and is still stable up to temperatures of about 300° C. Deposits of, for example, molecule groups such as $C_3H_7NH_2$ on the pore surfaces obviously result in a preferred affinity to substances from the class of amines. Furthermore such surface deposits have the additional advantage of not requiring special filter membranes, which are otherwise required by comparable sensor elements of the previous art. In a second embodiment, the layer of variable optical thickness is substituted by a porous dielectric organic layer which originally has a non-polar surface character. It is feasible to make such a porous polymer layer out of a mixture of polymerizable monomers and an inert organic solvent. The mixture is deposited on a substrate. A porous layer is produced by polymerization and subsequent removal of the inert solvent. Due to their outstanding optical transmission properties, methyl-methacrylate (MMA) or tri-ethylene-glycolic-dimethacrylate (TGMA) are utilized as a monomeric reactant, whereas octane is used as an inert solvent. Benzene peroxide can be used as a polymerization initiator. Subsequent to a complete polymerization and after removal of the inert solvent octane by washing with acetone, a porous polymeric layer is obtained which has the desired non-polar and hydrophobic surface, so that vaporous substances with non-polar molecules may condense in pores of the corresponding size depending on the vapor pressure. It is feasible to deliberately control the size and number of pores via the ratio of the mixture and the polymerization conditions. The thickness of the layer may be preselected to obtain optical effects desired by a particular application. To this end, it is additionally feasible to combine the layer with other ones to layer systems.

When more pores are required they can, of course, be produced by "irradiation processes", as common practice in microlithography, (for example, by electron irradiation) and subsequent developing. PMMA-layers conventionally used in electron beam lithography are particularly suited.

In a third embodiment, which can be optionally used in the applications disclosed hereinabove, the layer 31 of variable optical thickness is substituted by a dielectric layer which has no directly recognizable pore structure. However, it is capable to solve and, hence, absorb, for example, non-polar hydrocarbon compounds or such having small molecular dipole moments, which may be smaller than the dipole moment of water. In consequence thereof, variations of the optical refractive number and/or the thickness of the layer 31 result. However, water is not soluble in these layers in concentrations worth mentioning. The layer or the layers are required to be capable of integration in an optical filter-layer system or they are required to permit the setup of an optical filter-layer system. Typically, such layers consist of siloxanes, for example, di-methylpolysiloxane (DMPS) and of polytetrafluorethylene (for example, Teflon AF). In both substances, hydrocarbon compounds, particularly chlorinated hydrocarbons, are easily soluble, but water is hardly soluble. DMPS, having refractive numbers of 1.4 and slightly more, may take the function of an optically high refracting layer and Teflon AF, having a refractive number of about 1.3, which is the value of an optically low refracting layer so that an optical filter layer system can be set up by an alternating sequence of such layers, with adjustable optical thickness which corresponds to a quarter and to a half, respectively, of an optical working wavelength. When hydrocarbon molecules are absorbed by the layers, the optical effective thickness varies due to the refractive number and thickness variations dependent thereof, so that displacements of the optical working wavelength of the filter result, at which point maximum transmission or reflection takes place. It is feasible to evaluate the spectral displacements by respective measuring techniques-with a high precision and reliability.

The features disclosed in the specification, the subsequent claims, and the drawings are essentially for the invention individually, as well as in any combination.

We claim:

1. An optical sensor element for detecting an organic compound, comprising a spectral band filter having three layer systems including two reflecting interference layer systems acting as reflecting layers and an intermediate spacing layer consisting of a dielectric inorganic material having pores, the surfaces of the pores having a monomolecular coating of an organosilicon compound, said two reflecting interference layer systems being on opposite sides of said spacing layer, said spacing layer being an interference layer system of at least one layer having an optical thickness of $\lambda/4$ or $\lambda/2$ or an integral multiple of $\lambda/4$ or $\lambda/2$, wherein $\lambda$ is a mean working wavelength, and said monomolecular coating providing a group with an affinity for the organic compound to be detected, the optical thickness of said at least one layer of the spacing layer being changed by the formation in said pores of liquid condensate of the compound to be detected.

2. The optical sensor element of claim 1, wherein said spacing layer has at least two layers having alternating optical thicknesses of $\lambda/4$ or $\lambda/2$ or integral multiples thereof.

3. The optical sensor element of claim 1 or 2, wherein the dielectric inorganic material is a metal oxide which is hydrated at least at said surfaces of said cores and said coating consists of the product of reacting said hydrated metal oxide with an organosilane compound of the general chemical formula $R_zSiX_{(4-z)}$ with $1 \leq z \leq 4$, wherein X is a hydrolysable group and R is a non-hydrolysable organic group.

4. The optical sensor element of claim 3, wherein said hydrolysable group is selected from the group consisting of an alkoxy group and a halogen.

5. The optical sensor element of claim 1, wherein said organic compound to be detected is a hydrocarbon.

* * * * *